United States Patent
Spencer

(10) Patent No.: US 6,309,679 B1
(45) Date of Patent: Oct. 30, 2001

(54) METHOD OF IMPROVING PROCESSES USING PECTINASE ENZYMES WITH NOBLE GASES

(75) Inventor: Kevin C. Spencer, Hinsdale, IL (US)

(73) Assignee: American Air Liquide, Walnut Creek, CA (US)

( * ) Notice: Subject to any disclaimer, the term of this patent is extended or adjusted under 35 U.S.C. 154(b) by 0 days.

(21) Appl. No.: 08/378,091

(22) Filed: Jan. 25, 1995

Related U.S. Application Data

(63) Continuation of application No. 07/982,491, filed on Nov. 27, 1992, now abandoned.

(51) Int. Cl.$^7$ .................................................. C12G 1/00
(52) U.S. Cl. .................................. 426/15; 426/7; 426/49; 426/51; 426/312; 426/330.5
(58) Field of Search ............................... 426/7, 8, 11, 12, 426/15, 16, 29, 49, 50, 51–52, 118, 312, 313, 316, 319, 320, 330.3, 330.4, 330.5, 331, 333, 615, 616

(56) References Cited

U.S. PATENT DOCUMENTS

| | | |
|---|---|---|
| 2,569,217 | 9/1951 | Bagdigian . |
| 3,143,471 | 8/1964 | Coady . |
| 3,183,171 | 5/1965 | Schreiner . |
| 3,378,443 | 4/1968 | Cooper et al. . |
| 3,677,024 | 7/1972 | Segall . |
| 3,725,076 | 4/1973 | Stefanucci et al. . |
| 3,957,892 | 5/1976 | Kleiman . |
| 4,008,754 | 2/1977 | Kraushaar et al. . |
| 4,017,363 | 4/1977 | McMullen et al. . |
| 4,021,579 * | 5/1977 | Barrett .................... 426/11 |
| 4,044,004 | 8/1977 | Saucy et al. . |
| 4,136,049 | 1/1979 | Horiishi et al. . |
| 4,138,565 | 2/1979 | Ehrhardt et al. . |
| 4,259,360 * | 3/1981 | Venetucci et al. ................. 426/231 |
| 4,308,264 | 12/1981 | Conway et al. . |
| 4,314,810 | 2/1982 | Fourcadier et al. . |
| 4,315,266 | 2/1982 | Ellis, Jr. . |
| 4,329,433 * | 5/1982 | Seebeck et al. .................. 426/11 X |
| 4,450,960 | 5/1984 | Johnson . |
| 4,477,477 * | 10/1984 | Arter ................................. 426/330.4 |
| 4,496,397 | 1/1985 | Waite . |
| 4,501,814 | 2/1985 | Schoenrock et al. . |
| 4,548,605 | 10/1985 | Iwamoto et al. . |
| 4,622,425 | 11/1986 | Gagne . |
| 4,664,256 | 5/1987 | Halskov . |
| 4,812,320 | 3/1989 | Ruzek . |
| 4,830,858 | 5/1989 | Payne et al. . |
| 4,892,579 | 1/1990 | Hazelton . |
| 4,895,726 | 1/1990 | Curtet et al. . |
| 4,895,729 | 1/1990 | Powrie et al. . |
| 4,919,955 | 4/1990 | Mitchell . |
| 4,946,326 | 8/1990 | Schvester et al. . |
| 4,965,165 | 10/1990 | Saccocio et al. . |

(List continued on next page.)

FOREIGN PATENT DOCUMENTS

| | | |
|---|---|---|
| 989 311 | 5/1976 | (CA) . |
| 0635 601 | 9/1936 | (DE) . |
| 3 007 712 | 10/1981 | (DE) . |
| 0111 595 | 6/1984 | (EP) . |
| 0346 201 | 12/1989 | (EP) . |
| 0412 155 | 2/1991 | (EP) . |
| 0440 273 | 8/1991 | (EP) . |
| 1 339 669 | 9/1963 | (FR) . |
| 1 454 653 | 8/1966 | (FR) . |
| 2 156 559 | 6/1973 | (FR) . |
| 2 225 095 | 11/1974 | (FR) . |
| 2 261 518 | 9/1975 | (FR) . |
| 2 406 567 | 5/1979 | (FR) . |
| 2 643 232 | 8/1990 | (FR) . |
| 0415 656 | 8/1934 | (GB) . |
| 1 376 362 | 12/1974 | (GB) . |
| 2 029 846 | 3/1980 | (GB) . |
| 2 091 556 | 8/1982 | (GB) . |
| 52-27699 | 9/1972 | (JP) . |
| 52-86987 | 7/1977 | (JP) . |
| 52-97913 | 8/1977 | (JP) . |
| 54-129185 | 10/1979 | (JP) . |
| 1-059647 | 1/1980 | (JP) . |
| 58-39650 | 3/1983 | (JP) . |
| 58-107180 | 6/1983 | (JP) . |
| 60-56984 | 4/1985 | (JP) . |
| 63-77848 | 4/1988 | (JP) . |
| 2-104502 | 4/1990 | (JP) . |
| 3-200568 | 9/1991 | (JP) . |
| 1 289 437 | 2/1987 | (SU) . |

OTHER PUBLICATIONS

Federation Proceedings, vol. 26, No. 2, Mar.–Apr. 1967, pp. 650, G.F. Doebbler, et al., "Inert Gas Interactions and Effects on Enzymatically Active Proteins".

Febs Letters, vol. 62, No. 3, Mar. 1976, pp. 284–287, K. Sandhoff, et al., "Effect of Xenon, Nitrous Oxide and Halothane on Membrane–Bound Sialidase from Calf Brain".

Aviation, Space and Environmental Medicine, vol. 48, No. 1, Jan. 1977, pp. 40–43, S.K. Hemrick, et al., "Effect of Increased Pressures of Oxygen, Nitrogen, and Helium on Activity of A Na–K–Mg ATPase of Beef Brain".

Undersea Biomedical Research, vol. 17, No. 4, 1990, pp. 297–303, J.S. Colton, et al., "Effect of Helium and Heliox on Glutamate Decarboxylase Activity".

(List continued on next page.)

Primary Examiner—Leslie Wong
(74) Attorney, Agent, or Firm—Oblon, Spivak, McClelland, Maier & Neustadt, P.C.

(57) ABSTRACT

A method is provided for improving an enzymatic process using at least one enzyme having pectinase activity which entails contacting the at least one enzyme during the process with a noble gas, mixture of noble gases or gas mixture containing at least one noble gas.

23 Claims, 2 Drawing Sheets

U.S. PATENT DOCUMENTS

| | | |
|---|---|---|
| 4,971,813 | 11/1990 | Strobel et al. . |
| 5,004,623 | 4/1991 | Giddey et al. . |
| 5,006,222 | 4/1991 | Sequeria, Jr. . |
| 5,021,251 | 6/1991 | McKenna et al. . |
| 5,030,778 | 7/1991 | Ransford . |
| 5,045,529 | 9/1991 | Chiang . |
| 5,064,070 | 11/1991 | Higashiyama . |
| 5,108,656 | 4/1992 | Schvester et al. . |
| 5,128,160 | 7/1992 | Fath et al. . |

OTHER PUBLICATIONS

Sciences Des Aliments, vol. 4, No. 4, 1984, pp. 595–608, B. Pichard, et al., "Effect of Nitrogen, Carbon Monoxyde and Carbon Dioxyde on the Activity of Proteases of *Pseudomonas fragi* and *Streptomyces caespitosus*".

Chemical Abstracts, vol. 68, No. 14, AN–60751j, no date.
Chemical Abstracts, vol. 74, No. 23, AN–1212761, no date.
Chemical Abstracts, vol. 76, No. 13, AN–70898s, no date.
Chemical Abstracts, vol. 80, No. 7, AN–35579z, no date.
Chemical Abstracts, vol. 80, No. 11, AN–56112g, no date.
Chemical Abstracts, vol. 86, No. 3, AN–14672h, no date.
Chemical Abstracts, vol. 87, No. 22, AN–172800y, no date.
Chemical Abstracts, vol. 91, No. 17, AN–138183x, no date.
Chemical Abstracts, vol. 93, No. 24, AN–225670p, no date.
Chemical Abstracts, vol. 97, No. 18, AN–145890c, no date.
Chemical Abstracts, vol. 98, No. 10, AN–78191f, no date.
Chemical Abstracts, vol. 99, No. 21, AN–172397v, no date.
Chemical Abstracts, vol. 106, No. 25, AN–210601e, no date.
Chemical Abstracts, vol. 115, No. 20, AN–214644e, no date.
WPI Abstracts, AN–70–84762R, DE–1753586, no date.
WPI Abstracts, AN–82–05785E, DE–3 202 622, Sep. 9, 1982.
Federation Proceedings, vol. 27, No. 3, May–Jun. 1968, H.R. Schreiner, "General Biological Effects of the Helium–Xenon Series of Elements".
156 Food Technology, vol. 34, No. 6, Jun. 1980, pp. 102.

\* cited by examiner

METHOD OF IMPROVING PROCESSES USING PECTINASE ENZYMES WITH NOBLE GASES This application is a Continuation of application Ser. No. 07/982,491, filed on Nov. 27, 1992, now abandoned.

BACKGROUND OF THE INVENTION

1. Field of the Invention

The present invention relates to a method of improving processes using pectinase enzymes with noble gases.

2. Description of the Background

The ability of the noble gases helium (He), neon (Ne), argon (Ar), krypton (Kr), xenon (Xe) and radon (Ra) to enter into chemical combination with other atoms is extremely limited. Generally, only krypton, xenon and radon have been induced to react with other atoms, which are highly reactive such as fluorine and oxygen, and the compounds thus formed are explosively unstable. See *Advanced Inorganic Chemistry*, by F. A. Cotton and G. Wilkinson (Wiley, Third Edition). However, while the noble gases are, in general, chemically inert, xenon is known to exhibit certain physiological effects, such as anesthesia. Other physiological effects have also been observed with other inert gases such as nitrogen, which, for example, is known to cause narcosis when used under great pressure in deep-sea diving.

It has been reported in U.S. Pat. No. 3,183,171 to Schreiner that argon and other inert gases can influence the growth rate of fungi and argon is known to improve the preservation of fish or seafood. U.S. Pat. No. 4,946,326 to Schvester, JP 52105232, JP 80002271 and JP 77027699. However, the fundamental lack of understanding of these observations clearly renders such results difficult, if not impossible, to interpret. Moreover, the meaning of such observations is further obscured by the fact that mixtures of many gases, including oxygen, were used in these studies. Further, some of these studies were conducted at hyperbaric pressures and at freezing temperatures. At such high pressures, it is likely that the observed results were caused by pressure damage to cellular components and to the enzymes themselves.

For example, from 1964 to 1966, Schreiner documented the physiological effects of inert gases particularly as related to anesthetic effects and in studies relating to the development of suitable containment atmospheres for deep-sea diving, submarines and spacecraft. The results of this study are summarized in three reports, each entitled: "Technical Report. The Physiological Effects of Argon, Helium and the Rare Gases," prepared for the Office of Naval Research, Department of the Navy. Contract Nonr 4115(00), NR: 102-597. Three later summaries and abstracts of this study were published.

One abstract, "Inert Gas Interactions and Effects on Enzymatically Active Proteins," Fed. Proc. 26:650 (1967), restates the observation that the noble and other inert gases produce physiological effects at elevated partial pressures in intact animals (narcosis) and in microbial and mammalian cell systems (growth inhibition).

A second abstract, "A Possible Molecular Mechanism for the Biological Activity of Chemically Inert Gases," In: Intern. Congr. Physiol. Sci., 23rd, Tokyo, restates the observation that the inert gases exhibit biological activity at various levels of cellular organization at high pressures.

Also, a summary of the general biological effects of the noble gases was published by Schreiner in which the principal results of his earlier research are restated. "General Biological Effects of the Helium-Xenon Series of Elements," Fed. Proc. 27:872–878 (1968).

However, in 1969, Behnke et al refuted the major conclusions of Schreiner. Behnke et al concluded that the effects reported earlier by Schreiner are irreproducible and result solely from hydrostatic pressure, i.e., that no effects of noble gases upon enzymes are demonstrable. "Enzyme-Catalyzed Reactions as Influenced by Inert Gases at High Pressures." J. Food Sci. 34:370–375.

In essence, the studies of Schreiner were based upon the hypothesis that chemically inert gases compete with oxygen molecules for cellular sites and that oxygen displacement depends upon the ratio of oxygen to inert gas concentrations. This hypothesis was never demonstrated as the greatest observed effects (only inhibitory effects were observed) were observed with nitrous oxide and found to be independent of oxygen partial pressure. Moreover, the inhibition observed was only 1.9% inhibition per atmosphere of added nitrous oxide.

In order to refute the earlier work of Schreiner, Behnke et al independently tested the effect of high hydrostatic pressures upon enzymes, and attempted to reproduce the results obtained by Schreiner. Behnke et al found that increasing gas pressure of nitrogen or argon beyond that necessary to observe a slight inhibition of chymotrypsin, invertase and tyrosinase caused no further increase in inhibition, in direct contrast to the finding of Schreiner.

The findings of Behnke et al can be explained by simple initial hydrostatic inhibition, which is released upon stabilization of pressure. Clearly, the findings cannot be explained by the chemical-$O_2$/inert gas interdependence as proposed by Schreiner. Behnke et al concluded that high pressure inert gases inhibit tyrosinase in non-fluid (i.e., gelatin) systems by decreasing oxygen availability, rather than by physically altering the enzyme. This conclusion is in direct contrast to the findings of Schreiner.

In addition to the refutation by Behnke et al, the results reported by Schreiner are difficult, if not impossible, to interpret for other reasons as well.

First, all analyses were performed at very high pressure, and were not controlled for hydrostatic pressure effects.

Second, in many instances, no significant differences were observed between the various noble gases, nor between the noble gases and nitrogen.

Third, knowledge of enzyme mode of action and inhibition was very poor at the time of these studies, as were the purities of enzymes used. It is impossible to be certain that confounding enzyme activities were not present or that measurements were made with a degree of resolution sufficient to rank different gases as to effectiveness. Further, any specific mode of action could only be set forth as an untestable hypothesis.

Fourth, solubility differences between the various gases were not controlled, nor considered in the result.

Fifth, all tests were conducted using high pressures of inert gases superimposed upon 1 atmosphere of air, thus providing inadequate control of oxygen tension.

Sixth, all gas effects reported are only inhibitions.

Seventh, not all of the procedures in the work have been fully described, and may not have been experimentally controlled. Further, long delays after initiation of the enzyme reaction precluded following the entire course of reaction, with resultant loss of the highest readable rates of change.

Eighth, the reported data ranges have high variability based upon a small number of observations, thus precluding significance.

Ninth, the levels of inhibition observed are very small even at high pressures.

Tenth, studies reporting a dependence upon enzyme concentration do not report significant usable figures.

Eleventh, all reports of inhibitory potential of inert gases at low pressures, i.e., <2 atm., are postulated based upon extrapolated lines from high pressure measurements, not actual data.

Finally, it is worthy of reiterating that the results of Behnke et al clearly contradict those reported by Schreiner in several crucial respects, mainly that high pressure effects are small and that hydrostatic effects, which were not controlled by Schreiner, are the primary cause of the incorrect conclusions made in those studies.

Additionally, although it was reported by Sandhoff et al, FEBS Letters, vol. 62, no. 3 (March, 1976) that xenon, nitrous oxide and halothane enhance the activity of particulate sialidase, these results are questionable due to the highly impure enzymes used in this study and are probably due to inhibitory oxidases in the particles.

To summarize the above patents and publications and to mention others related thereto, the following is noted.

Behnke et al (1969), disclose that enzyme-catalyzed reactions are influenced by inert gases at high pressures. J. Food Sci. 34: 370–375.

Schreiner et al (1967), describe inert gas interactions and effects on enzymatically, active proteins. Abstract No. 2209. Fed. Proc. 26:650.

Schreiner, H. R. 1964, Technical Report, describes the physiological effects of argon, helium and the rare gases. Contract Nonr 4115 (00), NR: 102-597. Office of Naval Research, Washington, D.C.

Schreiner, H. R. 1965, Technical Report, describes the physiological effects of argon, helium and the rare gases. Contract Nonr 4115 (00), NR: 102-597. Office of Naval Research, Washington, D.C.

Schreiner, H. R. 1966, Technical Report, describes the physiological effects of argon, helium and the rare gases. Contract Nonr 4115 (00), NR: 102-597. Office of Naval Research, Washington, D.C.

Doebbler, G. F. et al, Fed. Proc. Vol.26, p. 650 (1967) describes the effect of pressure or of reduced oxygen tension upon several different enzymes using the gases Kr, Xe, $SF_6$, $N_2O$, He, Ne, Ar and $N_2$. All gases were considered equal in their effect.

Colten et al, Undersea Biomed Res. 17(4), 297–304 (1990) describes the combined effect of helium and oxygen with high pressure upon the enzyme glutamate decarboxylase. Notably, only the hyperbaric inhibitory effect of both helium and oxygen and the chemical inhibitory effect of oxygen was noted.

Nevertheless, at present, it is known that enzyme activities can be inhibited in several ways. For example, many enzymes can be inhibited by specific poisons that may be structurally related to their normal substrates. Alternatively, many different reagents are known to be specific inactivators of target enzymes. These reagents generally cause chemical modification at the active site of the enzyme to induce loss of catalytic activity, active-site-directed irreversible inactivation or affinity labeling. See *Enzymatic Reaction Mechanisms* by C. Walsh (W. H. Freeman & Co., 1979). Alternatively, certain multi-enzyme sequences are known to be regulated by particular enzymes known as regulatory or allosteric enzymes. See *Bioenergetics*, by A. L. Leninger (Benjamin/Cummings Publishing Co., 1973).

Pectinesterase (EC 3.1.1.11), endo-polygalacturonase (EC 3.2.1.15) and endo-pectin lyase (ED 4.2.2.10) are important pectic enzymes in fruit processing. Pectinesterase de-esterifies pectins producing methanol and pectic acid. PGA and pectin lyase are depolymerases which split glycosidic linkages in their preferred substrates. PGA hydrolyzes low esterified pectins. The combined action of PGA and pectinesterase can also depolymerize high methoxyl pectins.

These enzymes are used extensively in fruit processing, and are the critical determinants of ripening onset and rate in fruit storage and transport. Industrial applications may thus depend upon either externally applied enzymes or upon the enzymes naturally occurring in the product. Further, these enzymes have extremely widespread utility and the function and uses thereof described below are only for purposes of illustration and are not intended to be limitative.

For example, in various processing methods, such as the production of apple juice, pectinases are added to extracted juice to facilitate filtration and prevent gelling in concentrated juice, they are added to the pulp to improve press yield and they are added to liquify pulp.

The processed fruits may be further processed into jams, jellies, dried and rolled food products, pastes and many other products.

Fruit nectars have a high content of fruit ingredients, sugar and sometimes acid. An important factor of cloudy nectars (apricot, mango) is their cloudy stability. Pectic enzymes are used in stabilizing cloudy nectars. Polygalacturonase with added fungal Pectinesterase and polygalacturonase with added exo-arabanase or pure pectin lyase stabilize the cloud, prevent gelling and break cell walls.

Generally, in the ripening of fruit, several enzymes are involved in the degradation of cell walls. For example, PE (pectinesterase), PGA (polygalacturonase), PL (pectin lyase), PAL (pectic acid lyase) and changes in cell walls. These changes may be summarized below in Table 1.

| Tech. effects | Changes in cell walls | Active Enz. |
| --- | --- | --- |
| Firming: | Saponification of cell wall pectin | PE (+$Ca^{++}$) |
| Softening: | Limited degradation cell wall pectin | PGA, PL, PAL |
| Maceration: | Limited degradation middle lamella pectin organized tissue→cell suspension | |
| Disintegration: juice release cloud stabiliz. | Solubilization cell wall pectins and associated arabinans/galactans, cell wall fragmentation | PGA + PE, and/or PL + hemicellulases (arabanases, galactanases) |
| Liquefaction: | Solubilization of all cell wall polysaccharides | C + PE + PGA and/or PL |
| Saccharification: | Degradation of solubilized PS fragments to monosaccharides | Hemicellulases Oligomerases E × O – carbohydrases Glycosidases |
| Cloudy juices: cloud destabiliz. clarification | Saponification soluble/insoluble pectin Depolymerization soluble +insoluble pectin n reduction | inhibit. native PE PE + PGA, PL |

PE: Pectinesterase
PGA: Polygalacturonase
PL: Pectin lyase
PAL: Pectic acid lyase
C: Cellulase The above cell wall changes are fundamentally important in any fruit processing and ripening processes. Polygalacturonase:

Ripening of tomatoes: found in very low levels in green tomatoes, higher (600 x's) concentrations in ripe tomatoes.

Ripening of peaches: PGA activity found at the onset of ripening and increases sharply during ripening.

Ripening in other fruits: PGA activity is present in pears during the cell division stage, decreases during enlargement stage and markedly increases during ripening. PGA found in Papaya, ripe avocados, dates, ripe apples and mangoes. Also found in cucumbers.

In other plant tissue: carrot roots, citrus leaf explants, sealings of: corn, beans, oats and peas (also found in their stem and leaf tissue). (these are just a few examples).

At present, control of pectinesterases, pectinases, and polygalacturonases is not possible, except by manipulation of physical conditions and enzyme level, applied externally. However, an additional and more reliable means of control would be extremely useful to fruit processors, growers, and shippers.

SUMMARY OF THE INVENTION

Accordingly, it is an object of the present invention to provide a method of improving processes using pectinase enzymes with noble gases.

The above objects and others are provided by a method for improving processes using at least one enzyme having pectinase activity, which comprises contacting the at least one enzyme having pectinase activity during the process with a noble gas, mixture of noble gases or gas mixture containing at least one noble gas.

DETAILED DESCRIPTION OF THE PREFERRED EMBODIMENTS

Figure 1:
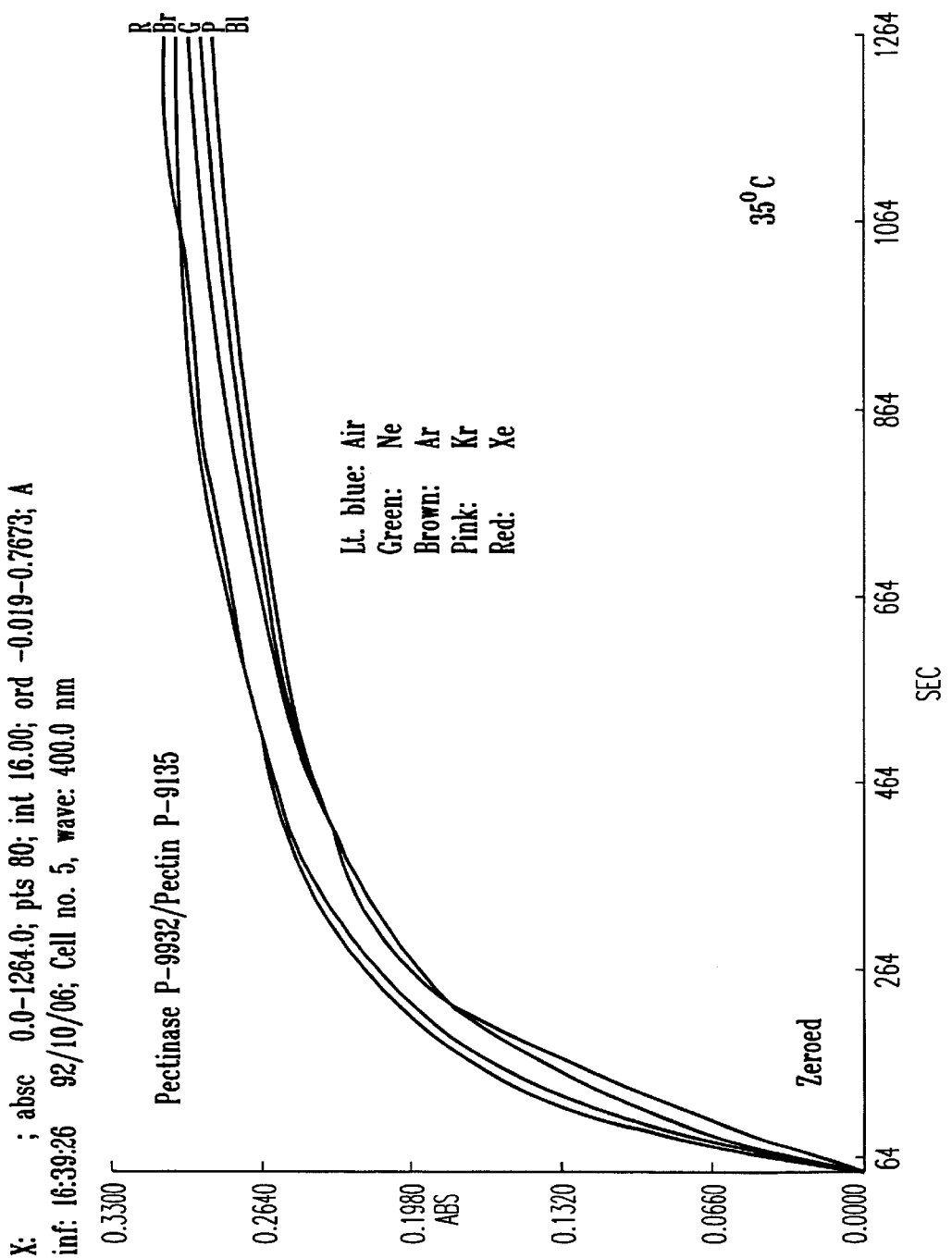
FIG. 1 illustrates the effect of Air, Ne, Ar, Kr and Xe on pectinase activity at 35° C.

In accordance with the present invention, it has been surprisingly discovered that noble gases may be advantageously used to control both the rates and yields of enzymes having pectinase activity. Thus, the present invention is most advantageously used with pectinase, pectinesterases and/or polygalacturonase activities. This affords a surprisingly useful means of controlling the ripening of fruits and vegetables during storage or transport or during processing of the same into processed foods.

Generally, the present invention may be used in any application where control of pectinase, pectinesterase and/or polygalacturonase activity is desired.

Thus, it has been discovered that application of argon, neon, krypton, or xenon, alone or in admixture with these or other gases, directly affects the activity of the enzymes pectinase, pectinesterase, and polygalacturonase. The maximum effects of each gas have been measured at a variety of temperatures, pressures, and other physical conditions. It has thus now become possible to control these enzyme activities in a predictable manner.

Thus, growers and shippers of fruit can directly control the stage of fruit ripening by simple application of noble-gas containing atmospheres.

Further, any pectinase, pectinesterase, or polygalacturonase-based process can be enhanced or inhibited through the selection of appropriate gas mixture and conditions of application. Such a process, for example, would be the control of ultimate pectin level and hence appearance cloudiness in fruit juices during and after processing.

Also, as used herein, the term "noble gas" is intended to include argon, xenon, krypton and neon. Helium does not work and radon is radioactive and, thus, not useful.

In accordance with the present invention, argon, xenon, krypton and neon may be used alone or in any combination. For example, binary mixtures of argon-xenon, krypton-xenon or xenon-neon may be used, or ternary mixtures of argon-xenon-krypton may be used, for example.

As noted above, a simple noble gas or mixture of noble gases may be used. However, mixtures containing at least one noble gas with one or more other carrier gases may also be used. Carrier gases may include, for example, nitrogen, oxygen, carbon dioxide, nitrous oxide and even helium.

Generally, the effect of the present invention may be obtained at a range of pressures form about near-vacuum, i.e., about $10^{-8}$ torr, to about 100 atmospheres. However, it is generally preferred that a pressure be used between about 0.001 to about 3 atmospheres. Further, a range of temperature is generally used which is the same as the operable and preferred temperatures of storage for beverages and edible oils and for different stages of processing. For example, such temperatures may range from freezing temperatures to cooking temperatures. However, lower temperatures and ambient temperatures are generally used for storage.

As noted above, a single noble gas, such as argon, or a mixture of noble gases may be used in accordance with the present invention. However, mixtures containing at least one noble gas and one or more carrier gases may also be used.

Any relative mix of the gases may be used as long as the preserving effect of the noble gas component or components outweighs any oxidative effects of the carrier gases, such as oxygen.

For example, in accordance with the present invention it is advantageous to use inexpensive production plant off-stream gases having a composition of about 90% Kr and 10% Xe in volume % based on the total gas volume or a Ne:He 1:1 mix.

It is also advantageous to use mixture containing an effective amount of one or more noble gases in deoxygenated air. Generally, as used herein, the term "deoxygenated air" is intended to mean air having generally less than 15 volume % or 10 volume %, preferably less than 5 volume % oxygen therein.

Generally, in accordance with the present invention, temperature is an important variable in the resultant effect. Further, the effect of the present invention is generally increased with increasing pressure. Moreover, it is surprisingly found that mixtures of a noble gases may be used with better than additive result.

In accordance with another aspect of the present invention, a method is provided for improving an enzymatic process using at least one enzyme having pectinase activity, which entails injecting a gas or gas mix into a reaction or process medium or media for the enzymatic process in containing means, or into containing means therefor, the gas or gas mixture comprising an element selected from the group consisting of argon, krypton, xenon, and neon and a mixture thereof; substantially saturating the reaction or process medium with the gas or gas mixture; maintaining the saturation substantially throughout the volume of the containing means and during substantially all the duration of the enzymatic process using the enzyme having pectinase activity.

It has been surprisingly discovered that if instead of solely blanketing the space above the reaction or process medium in a tank or other containing means with any inert gas, a gas or gas mixture containing an element selected from the group consisting of argon, krypton, xenon, neon, and a mixture thereof is sparged into the reaction or process medium and/or injected above the reaction or process medium in order to saturate or substantially saturate the reactionmedium with the gas or gas mixture, it is possible to substantially improve the extent of control over the enzymatic process, particularly when the saturation or substantial saturation is maintained throughout the volume of the storage container and during substantially all the duration of the enzymatic process.

The term "substantially saturate" means that it is not necessary to completely and/or constantly saturate the reaction medium with said gas or gas mixture (i.e., having the maximum amount of gas solubilized in said reaction or process medium). Usually, it is considered necessary to saturate the reaction medium to more than 50% of its (full) saturation level and preferably more than 70%, while 80% or more is considered the most adequate level of saturation of the reaction medium. of course, supersaturation is also possible. This means that if during the storage life of the reaction medium in the container, the reaction medium is not saturated with noble gas at least from time to time or even quite longer if it remains generally substantially saturated, results according to the invention are usually obtained. While it is believed that it is important that the entire volume of the container be saturated or substantially saturated with one of the above gas or a mixture thereof, it is quite possible to obtain the results according to the invention if a part of the volume is not saturated during preferably a limited period of time or is less saturated or substantially saturated than other portions of the volume of the reaction medium in the container.

While at least one of the above gases must be present in order to obtain the benefits of the invention, said gases can be diluted with some other gases, in order to keep for example the invention economically valuable. The diluent gases are preferably selected from the group comprising nitrogen, oxygen, nitrous oxide, air, helium or carbon dioxide. In case of an oxygen-containing gas or another reactive gas such as carbon dioxide, their degradative properties are such that these properties will mask the effect of noble gases, certainly in mixtures where they comprise 50% vol. or more and possibly 30% vol. or more. When those mixes comprise 0% to 10% vol. of these other gases, the noble gases referred to above are still extremely effective, while between 10% vol. and 20% vol. they are usually still effective, depending on the type of gases and conditions, which might be easily determined by the man skilled in the art.

In case of nitrogen and/or helium gas, the effect of noble gases consisting of Ar, Ne, Kr, Xe in the mixture is linearly proportional to its concentration in the mixture, which evidences that nitrogen and/or helium have no effect on substantially influencing the enzyme having pectinase activity. The mixture of noble gas and nitrogen and/or helium can thus comprise any amount (% volume) of nitrogen and/or helium: however, in practice, the lesser the proportion of noble gas selected from the group consisting of Ar, Ne, Kr and Xe, the larger the time required to achieve saturation or substantial saturation of the reaction medium.

Among the active gases (Ar, Kr, Xe, and Ne), it is preferred to use argon because it is cheaper than the other active gases. However, mixtures of argon and/or krypton and/or xenon are at least as effective as argon alone. It has also been unexpectedly found that mixtures comprising between 90 to 99% vol. argon and 1 to 10% Xe and/or Kr are usually the most effective as exemplified in the further examples (whether or not they are diluted with nitrogen, helium, or nitrous oxide). The difference in effect between the active gases defined hereabove and nitrogen have been also evidenced by the fact that mixtures of argon and oxygen or carbon dioxide have a similar (while decreased) effect than argon alone, while nitrogen mixed with oxygen or carbon dioxide evidenced no protective or preservative effect compared to oxygen or carbon dioxide alone.

Generally speaking, Xe is the most efficient gas according to the invention, followed by Kr, Ar and Ne. Among the suitable mixes, either pure or diluted with $N_2$, He, $N_2O$ (or even air, oxygen or a small amount of hydrogen) are the Ne/He mix comprising about 50% vol. of each, and the Kr/Xe mix comprising about 5–10% vol. Xe and about 90–95% vol. Kr, with a small amount of argon and/or oxygen (less than 2% vol.) or nitrogen (less than 1% vol.).

The temperatures at which the invention is carried out is usually between about 0C. to 60° C., and preferably about 10° C. and 30° C.

The injection of the gas or gas mixture into the reaction medium and/or into the container, e.g. by sparging is usually done at about 1 atmosphere but is still quite operable at 2 or 3 atmospheres, while saturation is increased at higher pressures. The pressure of the gas above the wine in the container shall be, in any case, preferably lower than 10 atmospheres and it is usually acceptable to maintain it lower than 3 atmospheres.

Saturation or substantial saturation of the reaction medium can be measured by various methods well-known by the man skilled in the art, including but not limited to thermogravimetric analysis or mass change weighting.

There are a variety of standard methods available for the detection, qualitative and quantitative measurement of gases, and several are especially well suited for the determination of degree of saturation of noble gases into liquid samples.

Samples generally are completely evacuated as a control for zero % saturation. Such samples may then be completely saturated by contact with noble gases such that no additional noble gas will disappear from a reservoir in contact with the sample. Such saturated samples may then have their gas content driven off by trapped evacuation or by increase in temperature, and said gas sample identified quantitatively and qualitatively. Analysis is of trapped gases, reservoir gases, or some other headspace of gases, not directly of the sample.

Direct sample analysis methods are available, and include comprehensive GC/MS analysis, or by mass or thermal conductance or GC analysis and comparison with calibrated standards.

The simplest method is GC/MS (gas chromatography/mass spectrometry), which directly determines gas compositions. By preparing a standard absorption curve into a given sample for a series of gases and mixtures, one can accurately determine the degree of saturation at any point in time.

GC/MS is applied to the gas itself, as in the headspace above a sample. The technique may be used either to determine the composition and quantity of gas or mixture being released from a sample, or conversely the composition and quantity of a gas or mixture being absorbed by a sample by following the disappearance of the gas.

Appropriate GC/MS methods include, for example, the use of a 5 Angstrom porous layer open tubular molecular sieve capillary glass column of 0.32 mm diameter and 25 meter length to achieve separation, isothermally e.g. at 75° C. or with any of several temperature ramping programs optimized for a given gas or mixture e.g. from 35–250° C., wherein ultra-high purity helium or hydrogen carrier gas is used at e.g. 1.0 cc/min flow rate, and gases are detected based upon their ionicity and quantitative presence in the sample, and characterized by their unique mass spectra.

Appropriate experimental conditions might include, for example, completely evacuating a given sample under vacuum to remove all absorbed and dissolved gases, then adding a gas or mixture to the sample and measuring a) the rate of uptake of each component as disappearance from the added gas, and/or b) the final composition of the gas headspace after equilibration. Both measurements are made by GC/MS, and either method can be used in both batch and continuous modes of operation.

A simplification of this analysis entails the use of a GC only, with a thermal conductivity detector, wherein adequate knowledge of the gas saturation process and preparation of calibration curves have been made such that quantification and characterization of gases and mixtures can be accomplished without mass spectral analysis. Such instruments are relatively inexpensive and portable.

A further simplification would depend solely upon measurement of the mass change in the sample upon uptake of various gases or mixtures, which depends upon the use of standard curves or absorption data available from the literature.

An alternate method for such mass measurements is thermogravimetric analysis, which is highly precise, wherein a sample is saturated with gas and mass changes are correlated to thermal change.

Having generally described the present invention, reference will now be made to certain examples which are provided solely for purposes of illustration and which are not intended to be limitative.

EXAMPLE 1

PECTINESTERASE (P-5400)/p-NITROPHENYL ACETATE (N-8130) GAS RUN PROTOCOL

PURPOSE: Effect of Air, Ne, Ar, Kr, Xe, $N_2$ and $O_2$ on Pectinesterase/p-Nitrophenyl acetate reaction at 10° C., 25° C. and 35° C. (one substrate concentration).
ENZYME: Pectinesterase P-5400
  (EC 3.1.1.11)
  Lot 51H8070
  from Orange Peel
  lyophilized powder containing approx. 35% protein; balance primarily buffer salts as $(NH_4)_2SO_4$ and sodium chloride
  74 mg solid
  205 units/mg solid
  Unit definition: one unit will release 1 μequivalent of acid from pectin per min at pH 7.5 at 30° C.
SUBSTRATE: p-Nitrophenyl acetate N-8130
  Lot 70H5012
  FW 181.1
SOLUTION PREPARATION:
  Soln A: 0.1 M Citric acid—$Na_2HPO_4$ buffer, pH 7.5 25° C.
    Dissolve 1.49 g citric acid and 13.10 g $Na_2HPO_4$ in 1 Liter DI $H_2O$. Adjust pH to 7.5.
  Soln B: 50 mM Methanolic p-Nitrophenyl acetate (N-8130)
    Dissolve 91 mg N-8130 in 10 ml methanol.
  Make this in a 10 cc amber vial.
    Refrigerate. LIGHT SENSITIVE.
  Soln C: p-Nitrophenyl acetate in Soln A
    Dilute 1 ml of Soln B to 50 ml with Soln A.
    This will have to be prepared for each temperature because of yellowing.
  Soln D: Pectinesterase (100 Units/ml) in Soln A
    Dissolve 24 mg P-5400 in 50 ml Soln A.
PARAMETERS:
  GASEOUS ATMOSPHERES:
    8 DIFFERENT GASEOUS ATMOSPHERES:
      →G1 Air
      G2 Ne
      G3 Ar
      G4 Kr
      G5 Xe
      →G6 Air
      G7 $O_2$
      G8 $N_2$
  TEMPERATURES:
    3 DIFFERENT TEMPERATURES:
      T1 10° C.
      T2 25° C.
      T3 35° C.
  BLANK:
    R=2.0 ml Soln C+0.5 ml Soln A
Sample Preparation and runs schedule:
  use blue silicone
  label silicone-sealed cuvettes (PEST(1–3)G(1–8)
  Fill the cuvettes with 2.0 ml of Soln C with a 1 cc syringe.
  Fill 8 serum vials with 5.0 ml of Soln D. Stopper and crimp to effect a gas tight system.
  Keep cuvettes and serum vials stoppered when they are not being gassed. Materials Needed:
  Cuvettes with blue silicone: 8×3 (G×T)

$$\frac{1 \text{ (blk)}}{25 \text{ cuvettes tot.}}$$

10 cc syringes
  30 cc syringes
  Serum vials (10 cc): 8 (w/5 ml Soln D)
  Needles: B–D 20G1 1/2
SPECTROPHOTOMETRIC STUDY
  PARAM: ABS
    Slit 1 nm
    Speed 1500 nm/min
    ASave Y
    APrint N
    BACKGROUND CORRECTION: 900–190 nm
  T1 RUNS (10° C.)
    CPRG: 5 CELLS (for first 5 gases then 3 cells)
      400 nm
      120 pts (30 minutes)
      Int 16 s
      $Y_{min}=0$
      $Y_{max}=2.0$
      Note: spectro chamber is flushed with a continuous flow of nitrogen during the 10° C. run to prevent atmospheric moisture from condensing on the cell walls (thus affecting ABS readings).
Set digital controller on 10° C. and Fisher circulator on 5° C. and high pump speed.

Bubble 4×30 cc of the appropriate gas in T1G1 . . . 5 cuvettes. Refrigerate under 2×10 cc of the appropriate gas. Keep refrigerated at least 15 minutes before running.

Bubble 4×30 cc of the appropriate gas in G1 . . . 5 serum vials. Refrigerate under 2×10 cc of the appropriate gas.

Remove the cuvettes from the refrigerator and remove the syringes/needles from the cuvettes. Tap cuvettes to eliminate bubbles. Wipe walls. Put cuvettes in cell holder. Allow cuvettes to come to temperature.

Remove G1 . . . 5 serum vials from fridge. Sample Soln D with 1 cc syringes previously filled with the appropriate gas. Slide the syringes/needle through the silicone but not into the liquid layer, simultaneously push plungers into the liquid and push the plungers simultaneously, run timedrives.

[PEST1G(1–5)] 30 min

Bubble 4×30 cc of the appropriate gas in T1G6 . . . 8 cuvettes. Refrigerate under 2×10 cc of the appropriate gas. Keep refrigerated at least 15 minutes before running.

Bubble 4×30 cc of the appropriate gas in G6 . . . 8 serum vials. Refrigerate under 2×10 cc of the appropriate gas.

Remove the cuvettes from the refrigerator and remove the syringe/needles from the cuvettes. Tap cuvettes to eliminate bubbles. Wipe walls. Put cuvettes in cell holder. Allow cuvettes to come to temperature.

Remove G6 . . . 8 serum vials from fridge. Sample Soln D with 1 cc syringes previously filled with the appropriate gas. Slide the syringes/needle through the silicone but not into the liquid layer, simultaneously push plungers into the liquid and push the plungers simultaneously, run timedrives.

[PEST1G(6–8)] 30 min

T2 RUNS (25° C.)
    CPRG: 5 CELLS (for first 5 gases then 3 cells)
        400 nm
        120 pts (30 minutes)
        Int 16 s
        $Y_{min}=0$
        $Y_{max}=2.0$ Set digital controller on 25° C. and Fisher circulator on 20° C. and high pump speed.

Bubble 4×30 cc of the appropriate gas in T2G1 . . . 5 cuvettes. Refrigerate under 2×10 cc of the appropriate gas. Keep refrigerated at least 15 minutes before running.

Bubble 4×30 cc of the appropriate gas in G1 . . . 5 serum vials. Refrigerate under 2×10 cc of the appropriate gas.

Remove the cuvettes from the refrigerator and remove the syringes/needles from the cuvettes. Tap cuvettes to eliminate bubbles. Wipe walls. Put cuvettes in cell holder. Allow cuvettes to come to temperature.

Remove G1 . . . 5 serum vials from fridge. Sample Soln D with 1 cc syringes previously filled with the appropriate gas. Slide the syringes/needle through the silicone but not into the liquid layer, simultaneously push plungers into the liquid and push the plungers simultaneously, run timedrives.

[PEST2G(1–5)] 30 min

Bubble 4×30 cc of the appropriate gas in T2G6 . . . 8 cuvettes. Refrigerate under 2×10 cc of the appropriate gas. Keep refrigerated at least 15 minutes before running.

Bubble 4×30 cc of the appropriate gas in G6 . . . 8 serum vials. Refrigerate under 2×10 cc of the appropriate gas.

Remove the cuvettes from the refrigerator and remove the syringes/needles from the cuvettes. Tap cuvettes to eliminate bubbles. Wipe walls. Put cuvettes in cell holder. Allow cuvettes to come to temperature.

Remove G6 . . . 8 serum vials from fridge. Sample Soln D with 1 cc syringes previously filled with the appropriate gas. Slide the syringes/needle through the silicone but not into the liquid layer, simultaneously push plungers into the liquid and push the plungers simultaneously, run timedrives.

[PEST2G(6–8)] 30 min

T3 RUNS (35° C.)
    CPRG: 5 CELLS (for first 5 gases then 3 cells)
        400 nm
        120 pts (30 minutes)
        Int 16 s
        $Y_{min}=0$
        $Y_{max}=2.0$ Set digital controller on 35° C. and Fisher circulator on 30° C. and high pump speed.

Bubble 4×30 cc of the appropriate gas in T3G1 . . . 5 cuvettes. Refrigerate under 2×10 cc of the appropriate gas. Keep refrigerated at least 15 minutes before running.

Bubble 4×30 cc of the appropriate gas in G1 . . . 5 serum vials. Refrigerate under 2×10 cc of the appropriate gas.

Remove the cuvettes from the refrigerator and remove the syringes/needles from the cuvettes. Tap cuvettes to eliminate bubbles. Wipe walls. Put cuvettes in cell holder. Allow cuvettes to come to temperature.

Remove G1 . . . 5 serum vials from fridge. Sample Soln D with 1 cc syringes previously filled with the appropriate gas. Slide the syringes/needle through the silicone but not into the liquid layer, simultaneously push plungers into the liquid and push the plungers simultaneously, run timedrives.

[PEST3G(1–5)] 30 min

Bubble 4×30 cc of the appropriate gas in T3G6 . . . 8 cuvettes. Refrigerate under 2×10 cc of the appropriate gas. Keep refrigerated at least 15 minutes before running.

Bubble 4×30 cc of the appropriate gas in G6 . . . 8 serum vials. Refrigerate under 2×10 cc of the appropriate gas.

Remove the cuvettes from the refrigerator and remove the syringes/needles from the cuvettes. Tap cuvettes to eliminate bubbles. Wipe walls. Put cuvettes in cell holder. Allow cuvettes to come to temperature.

Remove G6 . . . 8 serum vials from fridge. Sample Soln D with 1 cc syringes previously filled with the appropriate gas. Slide the syringes/needle through the silicone but not into the liquid layer, simultaneously push plungers into the liquid and push the plungers simultaneously, run timedrives.

[(PEST3G(6–8)] 30 min

SPECTRA FILES:

```
PEST1G1 . . . 5.SP
PEST1G6 . . . 8.SP
PEST2G1 . . . 5.SP
PEST2G6 . . . 8.SP
PEST3G1 . . . 5.SP
PEST3G6 . . . 8.SP 24 files
```

EXAMPLE 2

PECTINASE (EC 3.2.1.15) (P-9932)/PECTIN (P-9135) GAS RUN PROTOCOL

PURPOSE: Effect of Air, Ne, Ar, Kr, Xe, $N_2$ and $O_2$ on Pectinase/Pectin reaction at 10° C., 25° C. and 35° C. (one substrate concentration).

ENZYME: Pectinase (Sigma No. P-9932) from *Aspergillus niger* Solution in 25–45% glycerol (actual glycerol content on label)
  Unit Definition: one unit will liberate 1.0 μmole of galacturonic acid from polygalacturonic acid per min at pH 4.0 at 25° C.
  Lot 70H02921
368 ml
  8.4 mg prot./ml
  8.1 units/mg prot.

SUBSTRATE: Pectin (Sigma No. P-9135) from Citrus fruits
  100 g

SOLUTION PREPARATION:
  Soln A: 0.1 M Citric acid—sodium citrate, pH 4.0 at 25° C. Dissolve 7.6 g citric acid and 12.05 g sodium citrate in 1 liter of DI $H_2O$. Adjust pH to 4.0. $pH_{25°C.}$=4.013
  Soln B: 1% Pectin in DI $H_2O$ Boil 100 ml DI $H_2O$. Add 1 g pectin, stir by hand. Cover, boil for 2 minutes, stir by hand, boil for an additional 1 minute. Remove from heat and let cool for 10 minutes.
    Place 6–10 layers of butter muslin loosely over a 250 ml beaker and secure with a rubber band. Filter solution through the butter muslin. Let solution cool to room temperature then dilute back to 100 ml using graduation mark on beaker. Transfer to an amber bottle. Store at room temp.
  Soln C: Pectinase (50 U/ml) in Soln A Dilute 43.5 ml Pectinase to 50 ml with Soln A. Store in an amber bottle and refrigerate.

PARAMETERS:
  GASEOUS ATMOSPHERES:
    8 DIFFERENT GASEOUS ATMOSPHERES:
      →G1 Air
      G1 Ne
      G3 Ar
      G4 Kr
      G5 Xe
      →G6 Air
      G7 $O_2$
      G8 $N_2$

TEMPERATURES:
  3 DIFFERENT TEMPERATURES:
    T1 10° C.
    T2 25° C.
    T3 35° C.

BLANK:
  R=2.0 ml Soln B+0.5 ml Soln A

Sample Preparation and runs schedule:
  use blue silicone
  label silicone-sealed cuvettes (PECT(1–3)G(1–8))
  Fill the cuvettes with 2.0 ml of Soln B with a 1 cc syringe.
  Fill 8 serum vials with 5.0 ml of Soln C Stopper and crimp to effect a gas tight system.
  Keep cuvettes and serum vials stoppered when they are not being gassed.

Materials Needed:
  Cuvettes with blue silicone: 8×3 (G×T)

$$\frac{1 \text{ (blk)}}{25 \text{ cuvettes tot.}}$$

10 cc syringes
  30 cc syringes
  Serum vials (10 cc): 8 (w/5 ml Soln C)
  Needles: B–D 20G1 ½

SPECTROPHOTOMETRIC STUDY
  PARAM: AbS
    Slit 1 nm
    Speed 1500 nm/min
    ASave Y
    APrint N
    BACKGROUND CORRECTION: 900–190 nm
  T1 RUNS (10° C.)
    CPRG: 5 CELLS (for first 5 gases then 3 cells)
      400 nm
      120 pts (30 minutes)
      Int 16 s
      $Y_{min}$=0
      $Y_{max}$=2.0
      Note: spectro chamber is flushed with a continuous flow of nitrogen during the 10° C. run to prevent atmospheric moisture from condensing on the cell walls (thus affecting ABS readings).

Set digital controller on 10° C. and Fisher circulator on 5° C. and high pump speed.

Bubble 4×30 cc of the appropriate gas in T1G1 . . . 5 cuvettes. Refrigerate under 2×10 cc of the appropriate gas. Keep refrigerated at least 15 minutes before running.

Bubble 4×30 cc of the appropriate gas in G1 . . . 5 serum vials. Refrigerate under 2×10 cc of the appropriate gas.

Remove the cuvettes from the refrigerator and remove the syringes/needles from the cuvettes. Tap cuvettes to eliminate bubbles. Wipe walls. Put cuvettes in cell holder. Allow cuvettes to come to temperature.

Remove G1 . . . 5 serum vials from fridge. Sample Soln C with 1 cc syringes previously filled with the appropriate gas. Slide the syringes/needle through the silicone but not into the liquid layer, simultaneously push plungers into the liquid and push the plungers simultaneously, THEN IT WILL BE NECESSARY TO PULL AND PUSH PLUNGER FOUR TIMES TO EFFECT MIXING OF THE SUBSTRATE AND ENZYME IN THE CUVETTES, run timedrives.

[PECT1G(1–5)] 30 min

Bubble 4×30 cc of the appropriate gas in T.G6 . . . 8 cuvettes. Refrigerate under 2×10 cc of the appropriate gas. Keep refrigerated at least 15 minutes before running.

Bubble 4×30 cc of the appropriate gas in G6 . . . 8 serum vials. Refrigerate under 2×10 cc of the appropriate gas.

Remove the cuvettes from the refrigerator and remove the syringe/needles from the cuvettes. Tap cuvettes to eliminate bubbles. Wipe walls. Put cuvettes in cell holder. Allow cuvettes to come to temperature.

Remove G6 . . . 8 serum vials from fridge. Sample Soln C with 1 cc syringes previously filled with the appropriate gas. Slide the syringes/needle through the silicone but not into the liquid layer, simultaneously push plungers into the liquid and push the plungers simultaneously, THEN IT WILL BE NECESSARY TO PULL AND PUSH PLUNGER FOUR TIMES TO EFFECT MIXING OF THE SUBSTRATE AND ENZYME IN THE CUVETTES, run timedrives.

[PECT1G(6–8)] 30 min

T2 RUNS (25° C.)
CPRG: 5 CELLS (for first 5 gases then 3 cells)
400 nm
80 pts (20 minutes)
Int 16 s
$Y_{min}=0$
$Y_{max}=2.0$ Set digital controller on 25° C. and Fisher circulator on 20° C. and high pump speed.

Bubble 4×30 cc of the appropriate gas in T2G1 . . . 5 cuvettes. Refrigerate under 2×10 cc of the appropriate gas. Keep refrigerated at least 15 minutes before running.

Bubble 4×30 cc of the appropriate gas in G1 . . . 5 serum vials. Refrigerate under 2×10 cc of the appropriate gas.

Remove the cuvettes from the refrigerator and remove the syringes/needles from the cuvettes. Tap cuvettes to eliminate bubbles. Wipe walls. Put cuvettes in cell holder. Allow cuvettes to come to temperature.

Remove G1 . . . 5 serum vials from fridge. Sample Soln C with 1 cc syringes previously filled with the appropriate gas. Slide the syringes/needle through the silicone but not into the liquid layer, simultaneously push plungers into the liquid and push the plungers simultaneously, THEN IT WILL BE NECESSARY TO PULL AND PUSH PLUNGER FOUR TIMES TO EFFECT MIXING OF THE SUBSTRATE AND ENZYME IN THE CUVETTES, run timedrives.

[PECT2G(1–5)] 20 min

Bubble 4×30 cc of the appropriate gas in T2G6 . . . 8 cuvettes. Refrigerate under 2×10 cc of the appropriate gas. Keep refrigerated at least 15 minutes before running.

Bubble 4×30 cc of the appropriate gas in G6 . . . 8 serum vials. Refrigerate under 2×10 cc of the appropriate gas.

Remove the cuvettes from the refrigerator and remove the syringes/needles from the cuvettes. Tap cuvettes to eliminate bubbles. Wipe walls. Put cuvettes in cell holder. Allow cuvettes to come to temperature.

Remove G6 . . . 8 serum vials from fridge. Sample Soln C with 1 cc syringes previously filled with the appropriate gas. Slide the syringes/needle through the silicone but not into the liquid layer, simultaneously push plungers into the liquid and push the plungers simultaneously, THEN IT WILL BE NECESSARY TO PULL AND PUSH PLUNGER FOUR TIMES TO EFFECT MIXING OF THE SUBSTRATE AND ENZYME IN THE CUVETTES, run timedrives.

[PECT2G(6–8)] 20 min

T3 RUNS (35° C.)
CPRG: 5 CELLS (for first 5 gases then 3 cells)
400 nm
80 pts (20 minutes)
Int 16 s
$Y_{min}=0$
$Y_{max}=2.0$ Set digital controller on 35° C. and Fisher circulator on 30° C. and high pump speed.

Bubble 4×30 cc of the appropriate gas in T3G1 . . . 5 cuvettes. Refrigerate under 2×10 cc of the appropriate gas. Keep refrigerated at least 15 minutes before running.

Bubble 4×30 cc of the appropriate gas in G1 . . . 5 serum vials. Refrigerate under 2×10 cc of the appropriate gas.

Remove the cuvettes from the refrigerator and remove the syringes/needles from the cuvettes. Tap cuvettes to eliminate bubbles. Wipe walls. Put cuvettes in cell holder. Allow cuvettes to come to temperature.

Remove G1 . . . 5 serum vials from fridge. Sample Soln C with 1 cc syringes previously filled with the appropriate gas. Slide the syringes/needle through the silicone but not into the liquid layer, simultaneously push plungers into the liquid and push the plungers simultaneously, THEN IT WILL BE NECESSARY TO PULL AND PUSH PLUNGER FOUR TIMES TO EFFECT MIXING OF THE SUBSTRATE AND ENZYME IN THE CUVETTES, run timedrives.

[PECT3G(1–5)] 20 min

Bubble 4×30 cc of the appropriate gas in T3G6 . . . 8 cuvettes. Refrigerate under 2×10 cc of the appropriate gas. Keep refrigerated at least 15 minutes before running.

Bubble 4×30 cc of the appropriate gas in G6 . . . 8 serum vials. Refrigerate under 2×10 cc of the appropriate gas.

Remove the cuvettes from the refrigerator and remove the syringes/needles from the cuvettes. Tap cuvettes to eliminate bubbles. Wipe walls. Put cuvettes in cell holder. Allow cuvettes to come to temperature.

Remove G6 . . . 8 serum vials from fridge. Sample Soln C with 1 cc syringes previously filled with the appropriate gas. Slide the syringes/needle through the silicone but not into the liquid layer, simultaneously push plungers into the liquid and push the plungers simultaneously, THEN IT WILL BE NECESSARY TO PULL AND PUSH PLUNGER FOUR TIMES TO EFFECT MIXING OF THE SUBSTRATE AND ENZYME IN THE CUVETTES, run timedrives.

[PECT3G(6–8)] 20 min

SPECTRA FILES:

```
PECT1G1 . . . 5.SP
PECT1G6 . . . 8.SP
PECT2G1 . . . 5.SP
PECT2G6 . . . 8.SP
PECT3G1 . . . 5.SP
PECT3G6 . . . 8.SP 24 files
```

Example results:

FIG. 1 shows a typical result for a trial reaction of pectinase under various gases, which are Air, Ne, Ar, Kr and Xe at 35° C.

Figure 2:
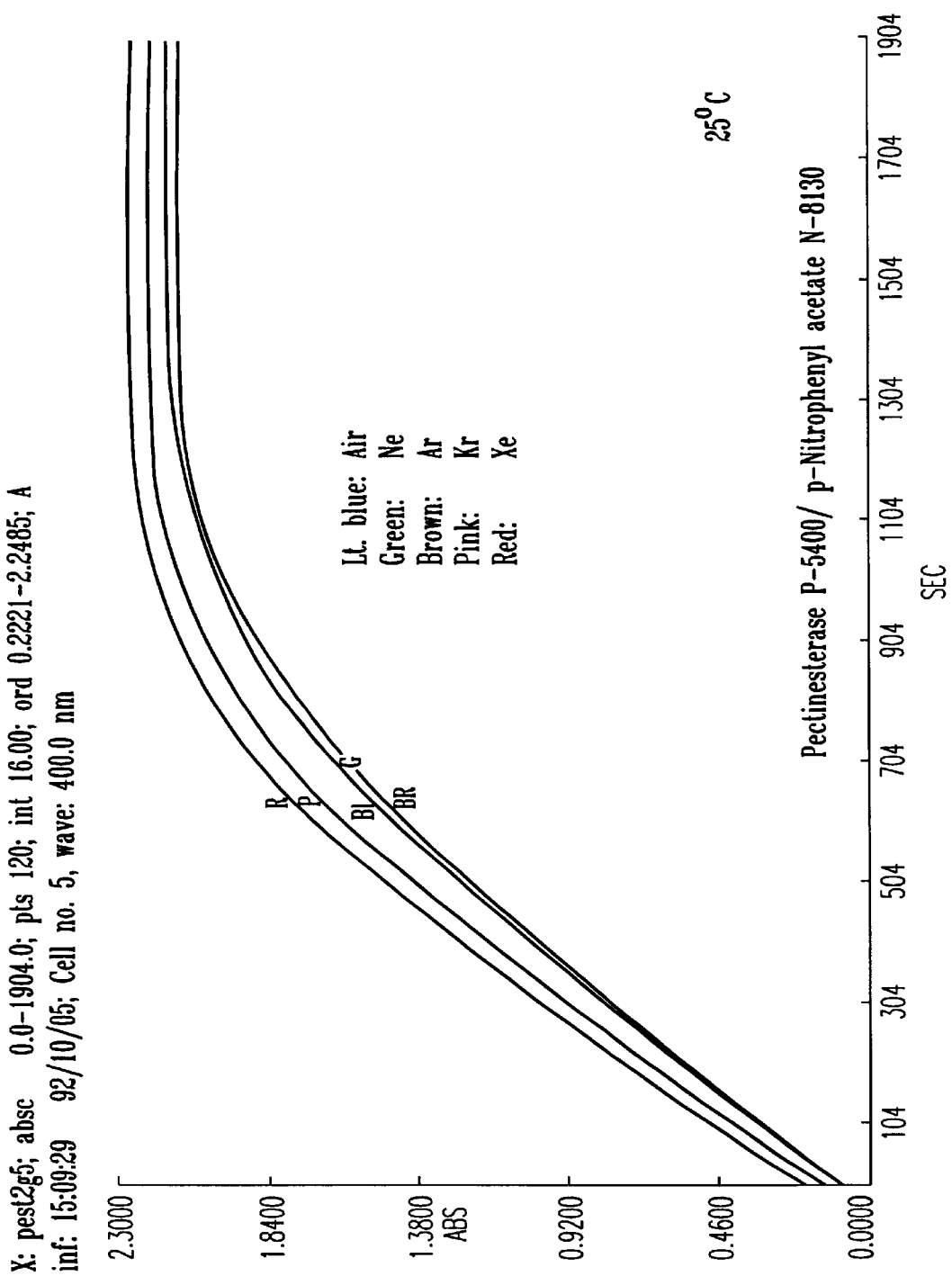
FIG. 2 illustrates the effect of Air, Ne, Kr and Xe on pectinesterase activity at 25° C.

FIG. 2 shows the results of a typical trial run of pectinesterase under various gases, which are Air, Ne, Ar, Kr and Xe at 25° C.

The Table below summarizes these results:

TABLE 1

Maximum effect of noble gases in changing activities of pectinase and pectinesterase. Percent change compared to air.

|  | Air | Ne | Xe | Ar | Kr |
|---|---|---|---|---|---|
| Pectinase % Rate Difference | | | | | |
| 25° C. | 0 | 4.3 | 0.0 | 6.4 | 2.1 |
| 35° C. | 0 | 3.3 | 15.0 | 18.3 | 6.7 |
| Pectinase % Yield Difference | | | | | |
| 35° C. | 0 | 3.3 | 7.0 | 8.0 | 1.4 |
| Pectinesterase % Rate Difference | | | | | |
| 10° C. | 0 | 19.4 | 29.0 | 5.0 | 32.3 |
| 25° C. | 0 | 0.0 | 2.0 | 17.7 | 29.4 |
| 35° C. | 0 | 1.6 | 3.3 | 0.8 | 0.8 |
| Pectinesterase % Yield Difference | | | | | |
| 25° C. | 0 | 0.37 | 0.70 | 2.1 | 8.3 |
| 35° C. | 0 | 1.4 | 0.0 | 0.70 | 2.1 |

Average, as compared to maximum observed differences in these trials, show the following.

Pectinesterase:

Pectinesterase activity is accelerated by the action of noble gases at all temperatures. An enhancement of both the rate and yield have been found at both optimal and non-optimal temperatures. Cold temperatures show the greatest enhancement by noble gases. Enhancement begins to decrease as the temperature approaches optimal temperatures. At higher temperatures enhancement of activity by noble gases is still observed.

Pectinase:

Pectinase activity is accelerated by action of noble gases at optimal and hot temperatures. An enhancement of both rate and yield were found at hot temperatures. Enhancement of rate was found at optimal temperatures. The amount of enhancement by noble gases was found to increase as the temperature increased from the optimum.

Having described the present invention, it will be apparent to one of ordinary skill in the art that many changes and modifications may be made to the above-described embodiments without departing from the spirit and the scope of the present invention.

What is claimed is:

1. A method for enhancing pectinase activity in an enzymatic process using at least one enzyme having pectinase activity, which comprises:
   a) injecting a gas into a fruit or fruit juice containing at least one enzyme having pectinase activity, the gas consisting essentially of argon, neon, krypton, xenon or a mixture thereof;
   b) saturating the fruit or fruit juice with the gas to an extent of at least 50% of full saturation of said fruit or fruit juice with said gas; and
   c) maintaining the saturation substantially throughout the fruit or fruit juice, and during said enzymatic process at a temperature of from 10 to 30° C. and at a pressure of less than 10 atm.

2. The method of claim 1, wherein said at least are enzyme is selected from the group consisting of pectinases, pectinesterases and polygalacturonases.

3. The method of claim 1, wherein said gas is injected in gaseous form or liquid form or both.

4. The method of claim 1, wherein said fruit or fruit juice is saturated to more than 70% volume of full saturation level.

5. The method of claim 4, wherein said fruit or fruit juice is saturated to more than 80% volume of full saturation level.

6. The method of claim 1, wherein said gas further comprises a carrier gas selected from the group consisting of nitrogen, oxygen, nitrous oxide, air, helium, carbon dioxide and a mixture thereof.

7. The method of claim 6, wherein said carrier gas is air, which is deoxygenated, thereby having a content of oxygen of less than 15 volume percent.

8. The method of claim 6, wherein said gas comprises less than 50% volume of oxygen, carbon dioxide or a mixture thereof.

9. The method of claim 6, wherein said gas comprises less than 30% by volume of oxygen, carbon dioxide or a mixture thereof.

10. The method of claim 6, wherein said gas comprises less than 20% volume of oxygen, carbon dioxide or a mixture thereof.

11. The method of claim 6, wherein said gas comprises less than 10% volume of oxygen, carbon dioxide or a mixture thereof.

12. The method of claim 1, wherein the gas comprises 90% to 99% volume of argon and 1% to 10% volume of xenon or 1% to 10% krypton.

13. The method of claim 1, wherein the gas comprises about 50% volume of neon and 50% volume of helium.

14. The method of claim 1, wherein the gas comprises about 5% to 10% volume of xenon and 90% to 95% volume of krypton.

15. The method of claim 1, wherein the gas comprises less than 2% volume of argon, oxygen, nitrogen or a mixture thereof.

16. The method of claim 1, wherein said enzymatic process is effected at a temperature between about 0° C. and 40° C.

17. The method of claim 16, wherein the temperature is between about 10° C. and 30° C.

18. The method of claim 1, wherein the gas is at a pressure of less than 3 atmospheres.

19. The method of claim 18, wherein the gas is at a pressure of between about 1 and 2 atmospheres.

20. The method of claim 1, wherein said gas is argon.

21. The method of claim 1, wherein said gas is neon.

22. The method of claim 1, wherein said gas is xenon.

23. The method of claim 1, wherein said gas is krypton.

\* \* \* \* \*